Aug. 1, 1944. J. C. BOWEN Plant Pat. 635
THORNLESS BLACKBERRY PLANT
Filed April 26, 1943
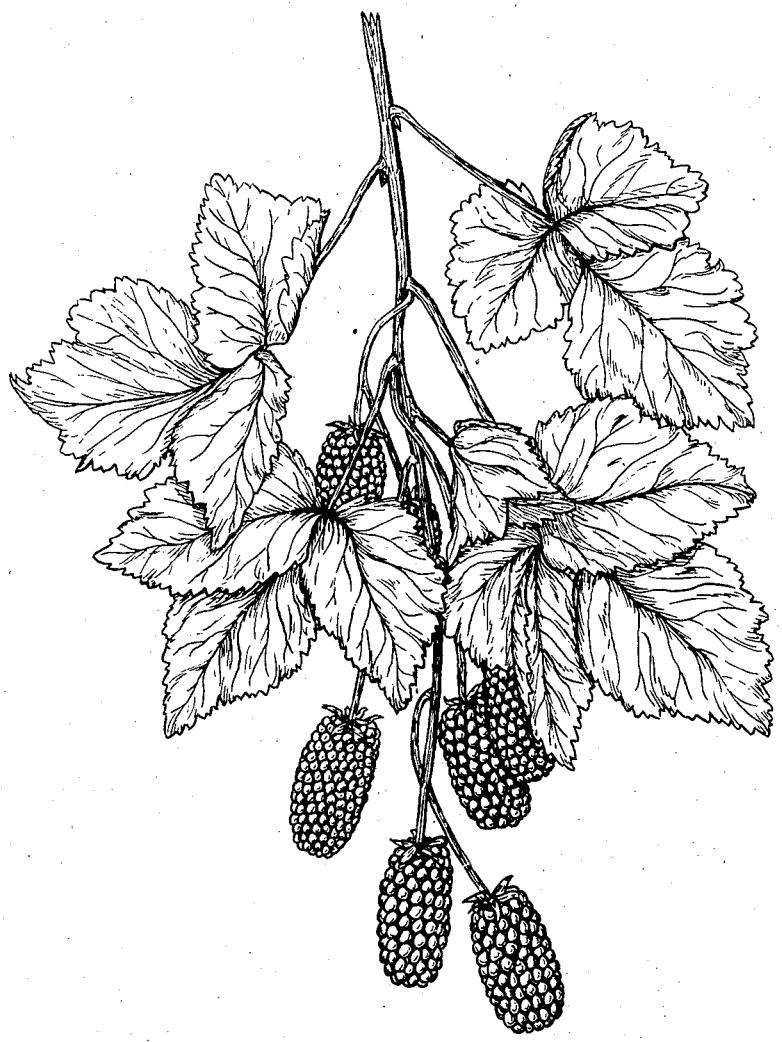
INVENTOR,
JOHN C. BOWEN.
BY
Chas. E. Townsend.
ATTORNEY.

Patented Aug. 1, 1944

Plant Pat. 635

UNITED STATES PATENT OFFICE

635

THORNLESS BLACKBERRY PLANT

John C. Bowen, Menlo Park, Calif.

Application April 26, 1943, Serial No. 484,563

1 Claim. (Cl. 47—62)

My invention relates to a new variety of blackberry, and more particularly to a new variety of thornless blackberry. The sport which I have discovered, and from which I have propagated my new plant, was discovered by me in a shady creek-bed thicket in the near vicinity of Burlingame, California. The thicket contained, among other things, a growth of black cap raspberries and Himalaya blackberries. I transplanted the sports to my property at Menlo Park, California, and soon discovered that the berry plants rejoiced in sunshine, although they grew well in the shade.

My plant resembles the black cap raspberry except that the cane and stems are entirely devoid of thorns. They are as thornless as a grapevine. My plant has the same characteristic of propagation in nature by contact of the cane tips with the soil, i. e., the cane tips slip themselves. I have planted, in the usual manner, about four thousand cuttings of the plant and have had nearly one hundred percent success therefrom. Owing to the fact that the plants grew true to the sport in respect to being thornless, I am assured that the thornless characteristics of the plant are permanent. One of the primary distinctions of my plant is that it does not send up any "suckers," and does not propagate from its roots. I planted well over 600 roots and never obtained a sprout. Other blackberry plants are noted for the numerous "suckers" which grow therefrom.

Another peculiarity of my plant is that "shoots" which develop into long vines grow out from the canes which have been cut to obtain slips. The "shoots" grow out several feet from the cane, flower and bear fruit and perpetuate the life of the cut cane. My plant is apparently very hardy and, of course, does not winterkill in California.

The plant is an extremely early bearer of fruit, blooming in the latter part of March and having berries an inch long shortly after the middle of April in California; and bears for quite a long period of time. The berry is very large and resembles that of the Nectar berry, except that it is much longer and usually bigger in diameter. The berry averages between 1 and 2 inches in length and between ¾ and 1 inch in diameter. I have found, however, berries as long as 2¼ inches. The berries are jet black and the drupelets are smaller than other blackberries. The berry seeds are extremely small, being somewhat similar to the Lawton blackberry in this respect. The berries may be eaten by persons having false teeth without difficulty.

The plant bears very heavily. I have found 186 fruit spurs on a cane about 12 feet long and each spur averaged at least 12 berries.

The flavor of the berry is similar to that of the Lucretia dewberry. Its taste might be said to be like a mixture of blackberry and red raspberry, being closer to the latter. The berries are very juicy and make excellent shortcake and pie.

A description of the plant, having reference to the accompanying drawing which forms a part hereof, is as follows:

The plant grows upwardly about four or five feet and then the canes bend over and grow outwardly from the hill 12 or more feet in length. It is not an upright berry plant like the Lawton blackberry. The canes are quite large and are reddish brown in color, the leaves are dark green and the fruit is jet black. The flowers are pink and white, similar in appearance to the black cap raspberry blooms except my plant's flowers are somewhat pink.

The fruit spurs grow from the vines at the junctures of the leaf stems and vine; every joint has a fruit spur from about two feet above the ground on up.

Having described my new discovery, what I claim and desire to secure by Letters Patent is:

A new variety of early bearing blackberry plant as herein shown and described, and characterized by a total absence of thorns, cane tip propagation, large, long, jet black berries, said berries having small drupelets, very small seeds, and the plant having the characteristic of not producing any "suckers."

JOHN C. BOWEN.